(12) United States Patent
Hummer (10) Patent No.: US 10,395,503 B2
(45) Date of Patent: Aug. 27, 2019

(54) MONITORING SYSTEM FOR USE WITH MOBILE COMMUNICATION DEVICE

(71) Applicant: Gregory J. Hummer, Shaker Heights, OH (US)

(72) Inventor: Gregory J. Hummer, Shaker Heights, OH (US)

(*) Notice: Subject to any disclaimer, the term of this patent is extended or adjusted under 35 U.S.C. 154(b) by 0 days.

(21) Appl. No.: 15/891,410

(22) Filed: Feb. 8, 2018

(65) Prior Publication Data

US 2018/0182223 A1 Jun. 28, 2018

Related U.S. Application Data

(63) Continuation of application No. 15/235,981, filed on Aug. 12, 2016, now Pat. No. 9,922,525.

(60) Provisional application No. 62/297,385, filed on Feb. 19, 2016, provisional application No. 62/205,012, filed on Aug. 14, 2015.

(51) Int. Cl.
| | |
|---|---|
| G08B 21/12 | (2006.01) |
| H04B 1/3888 | (2015.01) |
| H04M 1/725 | (2006.01) |
| G08B 25/10 | (2006.01) |
| G01N 33/00 | (2006.01) |
| G01N 33/497 | (2006.01) |
| H04M 1/21 | (2006.01) |

(52) U.S. Cl.
CPC ............ G08B 21/12 (2013.01); H04B 1/3888 (2013.01); H04M 1/7253 (2013.01); G01N 33/0009 (2013.01); G01N 33/4972 (2013.01); G08B 25/10 (2013.01); H04M 1/21 (2013.01)

(58) Field of Classification Search
CPC ...... G08B 21/12; G08B 25/10; H04B 1/3888; H04M 1/0202; H04M 1/7253; H04M 1/21; H04M 11/002; G01N 33/0009; G01N 21/7703; G01N 33/4972; B05D 5/061
See application file for complete search history.

(56) References Cited

U.S. PATENT DOCUMENTS

| | | |
|---|---|---|
| 7,176,793 B1 | 2/2007 | Hummer |
| 7,667,593 B1 | 2/2010 | Hummer |
| 7,911,336 B1 | 3/2011 | Hummer |
| D641,013 S | 7/2011 | Richardson et al. |
| 8,204,561 B2 | 6/2012 | Mongan et al. |
| 8,629,770 B2 | 1/2014 | Hummer et al. |
| 8,674,827 B2 | 3/2014 | Hummer |
| 8,930,341 B2 | 1/2015 | Amin et al. |
| 9,241,054 B1 * | 1/2016 | Roberts ............... H04B 1/3888 |
| 9,400,269 B2 | 7/2016 | Kambhampati |
| 9,466,057 B2 * | 10/2016 | Beeson ................. G06Q 20/32 |
| 9,922,525 B2 | 3/2018 | Hummer |

(Continued)

OTHER PUBLICATIONS

Article Application of Nanotechnology in Pesticides Removal from Aqueous Solutions—A review, T. Taghizade Firozjaee et al., Int. J. Nanosci. Nanotechnol., vol. 14, No. 1, Mar. 2018, pp. 43-56.

*Primary Examiner* — Leon Viet Q Nguyen
(74) *Attorney, Agent, or Firm* — Fay Sharpe LLP (57) ABSTRACT

A monitoring system for monitoring an environment and generating data in response to the presence of at least one chemical hazardous to human health in the environment. The monitoring system is configured to communicate the data to an associated personal communication device or the like for processing. The monitoring system can be in the form a selectively attachable component.

20 Claims, 6 Drawing Sheets

(56) References Cited

U.S. PATENT DOCUMENTS

| | | | |
|---|---|---|---|
| 2004/0119591 A1* | 6/2004 | Peeters | G08B 21/0222 |
| | | | 340/539.26 |
| 2006/0049714 A1* | 3/2006 | Liu | G01N 29/022 |
| | | | 310/313 R |
| 2014/0349707 A1* | 11/2014 | Bang | H04Q 9/00 |
| | | | 455/556.1 |
| 2014/0377130 A1 | 12/2014 | Edwards | |
| 2015/0180525 A1* | 6/2015 | Chen | H04B 5/0037 |
| | | | 455/575.8 |
| 2015/0326061 A1 | 11/2015 | Davison | |
| 2018/0038815 A1 | 2/2018 | Gu et al. | |
| 2018/0103206 A1* | 4/2018 | Olson | H04N 5/2252 |

* cited by examiner

MONITORING SYSTEM FOR USE WITH MOBILE COMMUNICATION DEVICE

CROSS REFERENCE TO RELATED PATENTS AND APPLICATIONS

This application is a continuation of U.S. patent application Ser. No. 15/235,981, filed Aug. 12, 2016, which claims the benefit of U.S. Provisional Patent Application Ser. No. 62/297,385, filed Feb. 19, 2016 and U.S. Provisional Patent Application Ser. No. 62/205,012, filed Aug. 14, 2015, which applications are hereby incorporated by reference.

BACKGROUND

The present exemplary embodiment relates to systems and methods for detecting chemicals. It finds particular application in conjunction with personal communication devices and/or other handheld or portable electronic devices, and will be described with particular reference thereto. However, it is to be appreciated that the present exemplary embodiment is also amenable to other like applications.

Cargo containers are widely used for shipping materials by land or by water from one country to another. Knowing the contents of such containers has become of increasing importance in detecting potential threats. It has thus become extremely important to monitor the contents of such containers for harmful materials, such as explosives, harmful biological and chemical materials, and radiation materials.

U.S. Pat. No. 7,176,793 discloses a detection device in the form of a strip for use in an enclosed container. The detection strip includes sensors of macro, meso or nanosize, all of which are referred to as nanosensors, for detecting materials that are harmful to human beings within an enclosed container and for transmitting a corresponding resonance frequency. One or more detection strips are initially placed within a container, depending on the size of the container. The detection devices are designed to send off specific resonant frequency signals which can be detected by voltage changes and/or current changes which are correlated to any harmful material detected within the container. A serial number computer chip is provided for specifically identifying the detection device and transmitting a corresponding resonance frequency, which allows the container to be identified. A power source is provided for operating the detection strip. A hand-held or stationary monitor is provided for monitoring the container for any signals given off from the detection strips within the container. The detection devices are designed to give off a predetermined amount of background signal. In consequence, if no such signals are received, the container is highly suspect as being tampered with, allowing such a container to be quickly removed and its contents examined.

BRIEF DESCRIPTION

The need to detect such chemicals goes far beyond shipping containers. It has been found to be desirable to monitor and detect certain chemicals in a variety of public spaces such as airports and other mass transit installations, stadiums, arenas, and/or any public or private space in general. Implementing monitoring systems in these locations presents challenges both in ensuring proper positioning and/or air flow to the sensors as well as facilitating monitoring of such sensors. Aspects of the present disclosure overcome one or more of such challenges.

In accordance with one aspect of the present disclosure, a monitoring system for monitoring an environment is disclosed. The monitoring system is operative to generate data in response to the presence of at least one chemical hazardous to human health in the environment and communicate the data to an associated personal communication device for processing, the monitoring system being selectively attachable to the associated personal communication device.

The monitoring system can include a detector component, communication circuitry and a power source operatively coupled to the detector component and the communication circuitry for supplying power thereto, and the communication circuitry can be configured to transmit data in response to detection of at least one chemical by the detector component. The power source can be at least one of a battery, a photovoltaic cell or an antenna for receiving electromagnetic energy. The monitoring system can be disposed in a protective case for a personal communication device. The protective case can be selectively attachable to an associated personal communication device. At least one of the detector component, communication circuitry or power source can be part of a removable/replaceable module selectively attachable to the protective case.

In accordance with another aspect, an assembly comprises a personal communication device having a processor and communication circuitry, and a device selectively attached to the personal communication device and having a monitoring system for monitoring an environment, the monitoring system operative to generate data in response to the presence of at least one chemical in the environment and communicate the data to the personal communication device. The processor of the personal communication device processes the data received from the device attached thereto to determine at least one of the kind or concentration of the at least one chemical in the environment.

The personal communication device can include a non-transitory computer readable medium storing instructions causing the processor to execute an application for processing the data, the application configured to: receive the data from the device, and analyze the data to detect one or more chemical signatures.

The device attached to the personal communication device can include a protective case. The protective case can include a resilient material for cushioning the personal communication device. The monitoring system can include a detector component, communication circuitry and a power source. At least one of the detector component, communication circuitry or power source can be part of a removable/replaceable module selectively attachable to the protective case. The power source can be at least one of a battery, a photovoltaic cell or an antenna for receiving electromagnetic energy.

In accordance with another aspect, a method of detecting a chemical comprises generating data with a device attached to a personal communication device, the device having a monitoring system for monitoring an environment, the monitoring system operative to generate data in response to the presence of at least one chemical in the environment, communicating the data to a personal communication device, and analyzing the data with the personal communication device to detect one or more chemical signatures.

The method can further include selectively attaching and removing the device to/from the personal communication device. Communicating the data to the personal communication device can be performed wirelessly, such as by using at least one of WIFI, Bluetooth, NFC or other wireless communication protocol.

DETAILED DESCRIPTION

Figure 1:
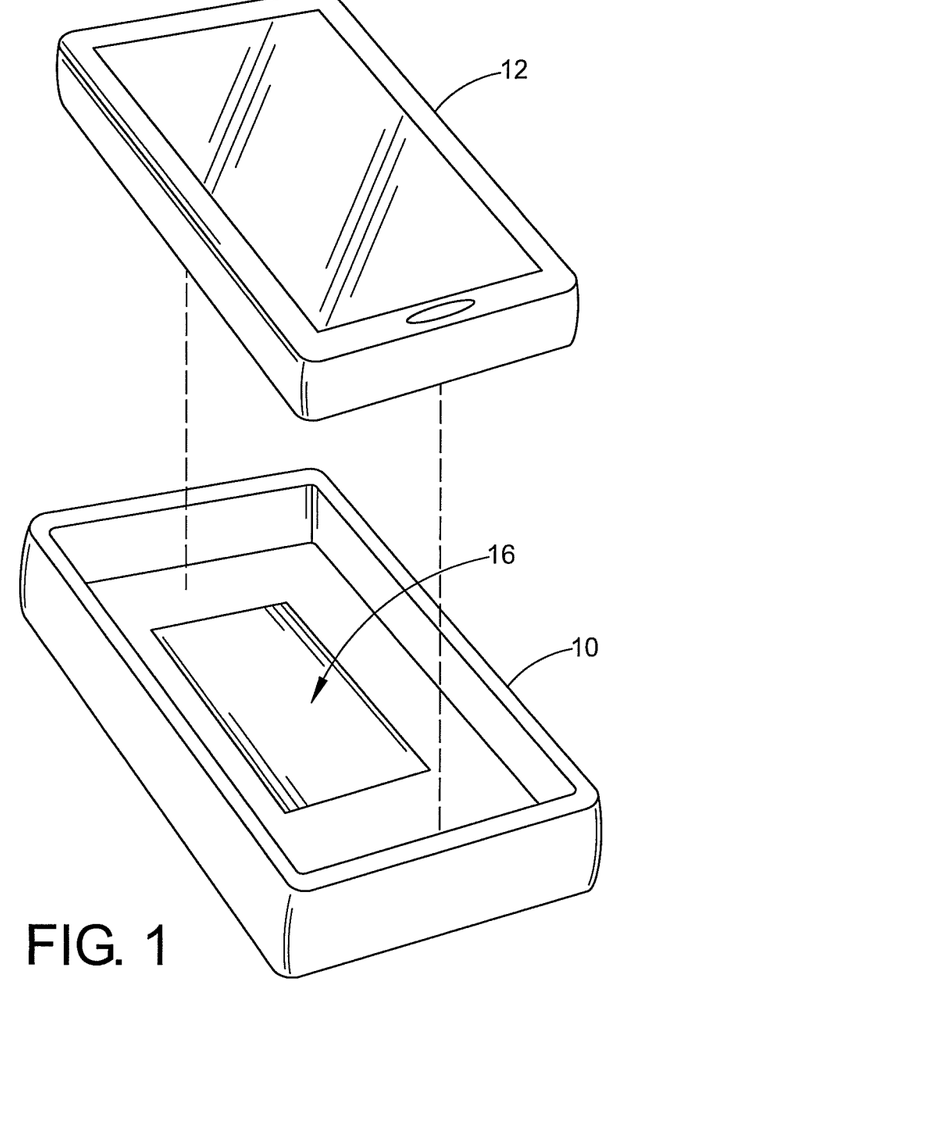
FIG. 1 illustrates a perspective view of an exemplary communication device and removable component in accordance with the present disclosure.

With reference to FIG. 1, an exemplary monitor for monitoring and detecting chemical compositions is illustrated and identified generally by reference numeral 10. In this embodiment, the monitor 10 is in the form of a protective case for a cell phone 12 or other personal communications device (e.g., tablets, laptops, etc.). It will be appreciated that the present disclosure is not limited to any particular case design or configuration, and that aspects of the disclosure can be embodied in a wide variety of both protective cases as well as ornamental cases and/or other devices attachable to either such cases or directly to a personal communication device. In other embodiments, aspects of the disclosure can be embodied in other types of accessories that may commonly be used with a cell phone or person communications device. For example, wearable devices such as smart watches, peripheral devices such as Bluetooth speakers, etc.

Returning to FIG. 1, the cell phone 12 is configured to be received in and/or at least partially surrounded by the case 10 in any suitable fashion. In some arrangements, the case may be made of a resilient material that can be deformed to allow the cell phone 12 to be securely inserted and retained within the case. In other arrangements, the case can include a hard plastic two-piece frame between which the cell phone 12 is sandwiched. Again, a wide variety of case designs and types are envisioned. The case 10 further includes a monitor system, which in FIG. 1 is identified by reference numeral 16.

Figure 2:
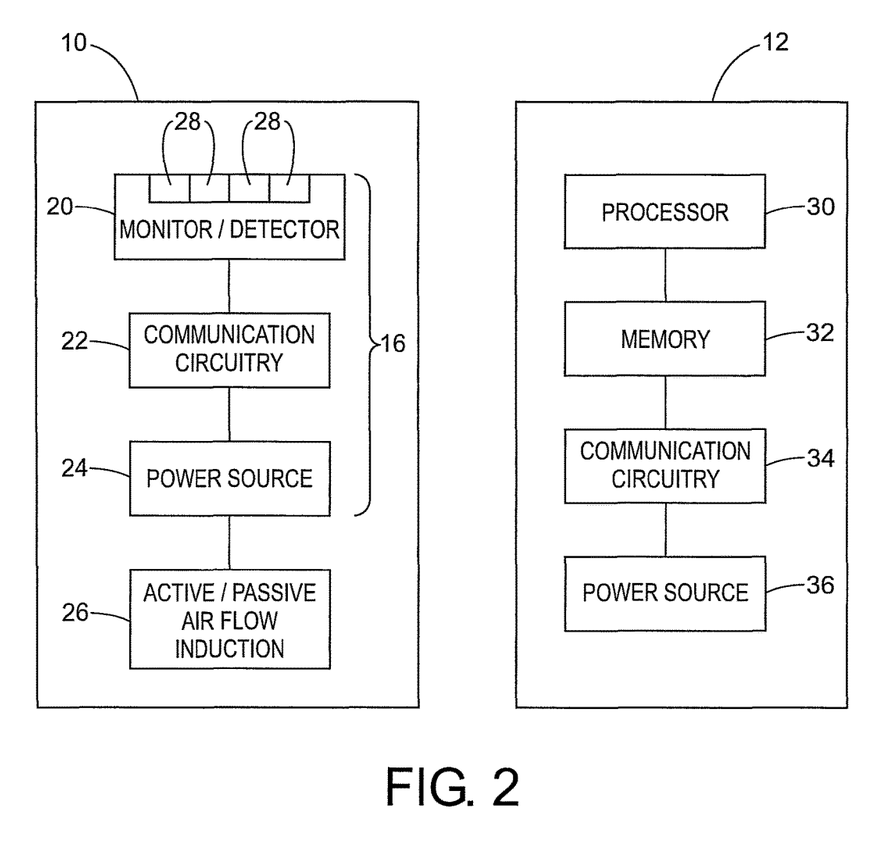
FIG. 2 illustrates a block diagram of an exemplary system in accordance with the present disclosure.

With reference to FIG. 2, the monitor system 16 generally includes a monitor/detector component 20. One monitor/detector component that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of monitor/detector components can also be used in accordance with the present disclosure.

The monitor system further includes communication circuitry 22 and a power source 24. The communication circuitry 22, in one embodiment, includes at least one of a near field communication device, Bluetooth communication device, WIFI communication device, or any other suitable communication circuitry for establishing communications with the cell phone 12. The power source 24 can be a power supply such as a battery (lithium or other) mounted or otherwise contained within case 10. In other embodiments, the power source 24 can be an antenna configured to receive energy wirelessly and supply the received energy to one or both of the monitor/detector component 20 and/or communication circuitry 22 such that no onboard battery is required for operation of the monitor system 16. In still other arrangements, the power source 24 can be a connector configured to couple with a port of the cell phone 12 to receive power from a power source of the cell phone 12.

An active or passive air flow induction device 26 can be provided for ensuring adequate and or continuous flow of air to the monitor 20. Such devices can include fans, micropumps, louvers, vents etc. An active induction device can be separately replaceable within the system and can include its own power supply. Alternatively, an active induction device can be configured to receive power from power supply 24.

It should be appreciated that the monitor/detector component 20 can comprise a plurality of sensors 28. The sensors 28 can be individually replaceable or can be replaced as a unit. Replacement of the sensors may be necessary due to sensor degradation. In other situations, a user may wish to detect certain chemicals and will choose which sensors to install in the system. In one embodiment, the entire monitor system 16 is replaceable as a unit.

The sensors 28 may detect harmful materials, such as explosives, radioactive materials, harmful chemicals, such as chemical warfare agents, nerve gases, biological materials, such as gases, anthrax and other germ warfare agents, narcotics and other illegal drugs, or combinations thereof. At least one of the sensors 28 can be configured for generating a signal which is indicative of the presence of a nitrogen-based explosive, such as trinitrotoluene (TNT) and/or a peroxide based explosive, such as triacetone triperoxide (TATP) or hexamethylenetriperoxidediamine (HMTD), or a combination thereof, for example.

It will be appreciated that the monitor system 16 is configured to communicate with the cell phone 12. That is, the monitor system 16 collects data and transmits or otherwise shares the collected data with the cell phone 12 for processing. The cell phone 12 of the illustrated embodiment includes a processor 30, a memory 32, a communication circuitry 34, and a power source 36. It will be appreciated that the cell phone 12 can include a wide variety of additional components as is conventional. Such additional components can include a display device, input device, various sensors, various antennas, etc.

Data collected by the monitor/detector 20 is transmitted via communication circuitry 22 to communication circuitry 34 of the cell phone 12. Other data, such as sensor state, status, performance data, and the like can also be transmitted to the cell phone 12. Any suitable manner of transmitting the data from the monitor system 16 to the cell phone 12 can be employed.

The data collected and transmitted by the monitoring system 16 is then processed by the phone to detect one or more chemicals in accordance with one or more methods set forth in U.S. Pat. No. 8,629,770 to Hummer et al. and U.S. Pat. No. 7,176,793 to Hummer. To this end, suitable software for analyzing the data is stored in memory 32 of the cell phone 12. Other detection and/or analyzing methods and techniques may also be used in conjunction with aspects of the present disclosure.

In one embodiment, the software stored in memory 12 can be in the form of an application, or "app", that is downloaded from an app store or the like. The app can be provided with various "signatures" of chemicals. The signatures can be compared to the data to determine whether the chemical signature was detected by the monitoring system 16. The app can be configured to be automatically updated with new signatures as the need to detect particular chemicals arise. That is, it is possible to provide new and/or additional chemical signatures for the app to check against the data to detect specific chemicals.

The app can further include features such as adjustable thresholds. For example, for some chemicals that are routinely present in certain amounts and/or not generally considered dangerous below certain levels, the application can be configured to detect or trigger an alarm when a threshold amount is met or exceeded. For some chemicals which are considered dangerous in any amount, the thresholds would not generally be adjustable.

The app can be further configured to, once a chemical is detected, share the detection information. For example, the application can be configured to use the communication circuitry 34 to broadcast an alert (or generate a notification) via any suitable communications network (e.g., WIFI, NFC, Bluetooth, cell, etc.). The alert may be directly sent to other cell phones and/or personal communication devices in the area, or may be sent to a server (or through a network) and then on to devices within a range of a given location. Accordingly, the application can be configured to use location information from a GPS chip, WIFI or any other location information available to the cell phone 12 to identify the location of the detected chemical.

The app can be configured to alert the authorities in the event certain chemicals are detected. For example, the detection of any amount of sarin gas (or other chemical/biological weapon) can trigger information relating to the location, time, etc. of the detection to be forwarded to certain designated authorities for threat management/mitigation.

It should be appreciated that a network of devices having monitoring systems, each detecting a certain chemical, can be configured to share valuable data regarding the dispersion of the particular chemical. For example, devices in close proximity to each other and the point of origin of the chemical may detect a greater concentration of the chemical than devices further away from the point of origin. Using this data and an appropriate dispersion model, a point of origin can be calculated. This can allow responsive action to be taken more quickly than otherwise would be the case.

Similarly, the data (location, concentration, etc.) from a plurality of such devices can be used to predict dispersion of the chemical so that preemptive action can be taken to minimize exposure of humans to the detected chemical.

Providing the monitoring system 16 in a separate component that is attachable to a phone or other personal communication device has several advantages. For example, any and all such devices can become monitors/detectors upon the provision of a suitable case or other component. Accordingly, a consumer can decide whether to add the functionality. In addition, the orientation, location and other aspects of the positioning of the sensor elements within the case or other component can be standardized to provide more consistent detection as compared to placing the sensor elements within various different models of cell phones. This is because the myriad phone manufacturers and models each have different space constraints that would dictate different available locations, orientations, etc. for the sensor elements within the phone. As such, some sensor elements would be in a better position within a respective phone to detect chemicals than other phones. This can lead to widely varying detection accuracy between different phones exposed to the same concentration of a given chemical.

It should be appreciated that, although the monitoring system 16 is illustrated as part of a case 10, the monitoring system can also be provided as a separate unit attachable either directly to a cell phone or the like, or attachable to a case in which a cell phone is contained.

Figure 3:
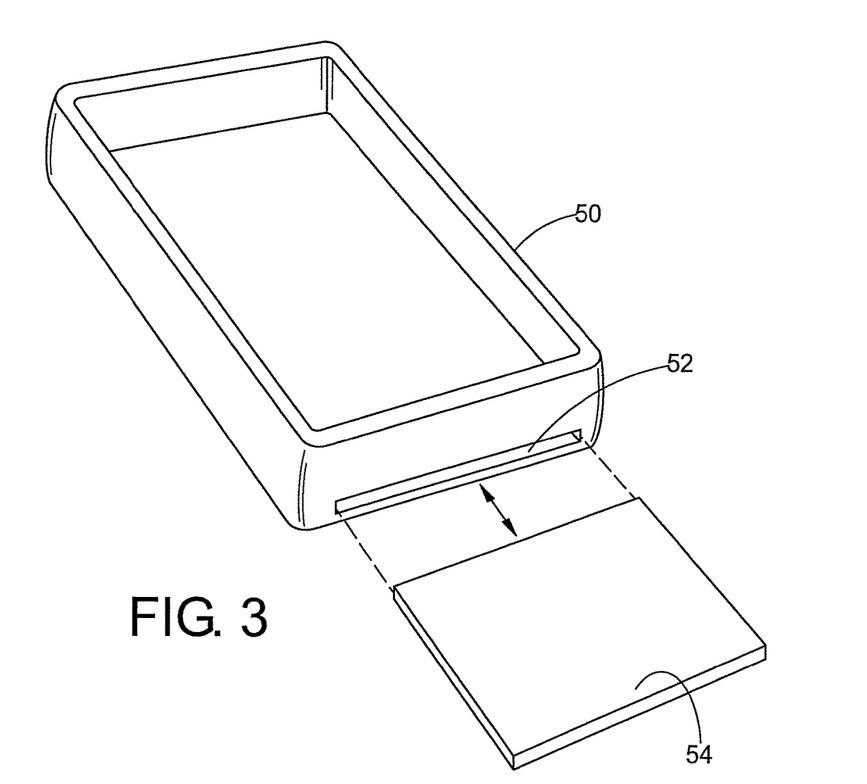
FIG. 3 illustrates another exemplary removable component in accordance with the present disclosure.

With reference to FIG. 3, another exemplary embodiment is illustrated and includes a case for a personal communication device identified generally by reference numeral 50. In this embodiment, the case 50 is similar to the case 10 of FIG. 1 but further includes a slot 52 for receiving a removable and/or replaceable monitoring system 54. In one embodiment, the removable/replaceable component includes all of the components of the monitoring system such as a power source, monitor/detector components, and communications circuitry. In other embodiments, the removable/replaceable component can include only the sensors of the monitor/detector, only the power source, only the communication circuitry, or any combination thereof. The removable/replaceable component can be configured to "click-lock" in the slot 52 in a manner similar to an SD card or the like wherein the component is pressed into the slot until a latch engages to retain the component and then pressed further into the slot to release the latch for removal. It will be appreciated that there are a wide variety of ways to retain the removable component in the slot. A seal or weatherproof cap can be provided to prevent ingress of water or contaminants.

While the foregoing embodiments illustrate a monitoring system attachable to a personal communication device directly or via a protective case or the like, it should be appreciated that the monitoring system of the above described embodiments can also link to the personal communication device without being physically attached thereto. Thus, the monitoring system can be provided as a standalone system to which the personal communication device can be configured to connect to perform the above described functions.

Figure 4:
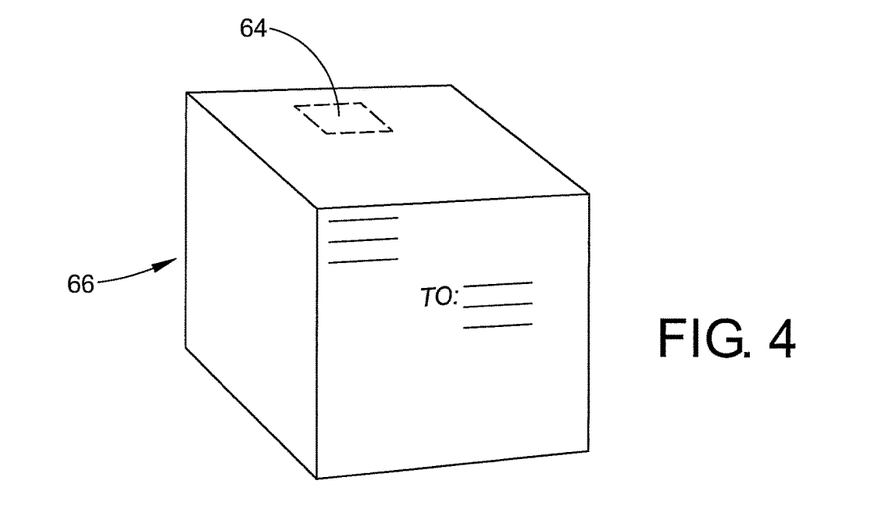
FIG. 4 illustrates an exemplary container including a monitoring system in accordance with the present disclosure.

For example, with reference to FIG. 4, a monitoring system 64 is provided in a separate container 66, such as a shipping box or the like. When the personal communication device is placed in proximity to the shipping box, the monitoring system can be configured to connect a personal communication device, such as cell phone 12, and perform the above-described functionality. The monitoring system can be placed inside the box, for detecting chemicals carried within the box, for example. In other embodiments the monitoring system 64 can additionally or alternatively monitor for chemicals outside of the box.

It should be appreciated that the monitoring system 64 can be configured to communicate with other devices besides (or in addition to) the personal communication device described above. Such devices can include scanners or other devices adapted to connect and receive data from a plurality of such monitoring systems disposed in a plurality of respective containers.

In one example, a scanning device can be associated with a conveyor system of a parcel service for scanning packages by communicating with monitoring systems associated with the packages as they advance through a shipping facility. In another example, the monitoring devices of the present disclosure can be associated with luggage (or other airline or common carrier freight). It will be appreciated that a wide variety of applications for the technology of the present disclosure are contemplated.

In some embodiments, it can be advantageous to include active and/or passive air flow inducing devices for ensuring sufficient air flow across the sensors. This can be particularly advantageous for applications wherein the sensors are in a fixed location, such as within a cargo hold or other location. Suitable devices can include fans or micropumps for displacing air across and/or adjacent a sensor installation. In some applications, louvers or vent openings can be positioned to maximize air flow to the sensor. Increasing air flow can make detection of certain chemicals more efficient.

It should be appreciated that the monitoring system 16 of the present disclosure can be configured to activate sensors 28 only when connected to a personal communication device or the like. In such configuration, the monitoring system generally lies dormant until such time as a connection is made with a remote device. The system 16 may then begin sensing for one or more chemicals and transmitting data to the remote device.

In another configuration, the system 16 may be configured to periodically activate to sense for the presence of one or more chemicals regardless of whether the system 16 is connected to a remote device. In this case, once the system 16 connects to a remote device, all past data gathered by the system 16 can be transmitted to the remote device to provide a sensing history.

Figure 5:
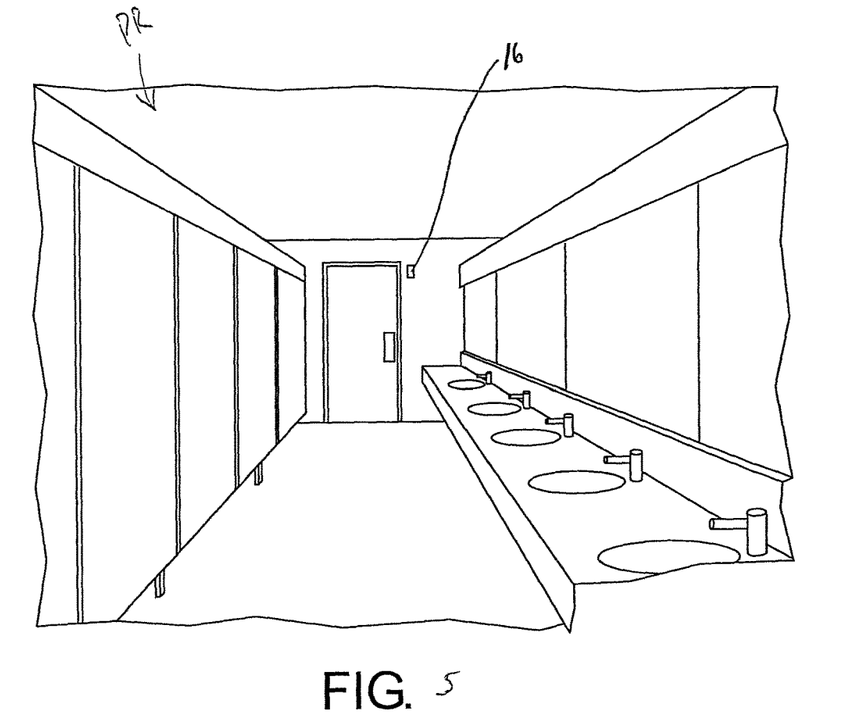
FIG. 5 illustrates an exemplary public space in which the monitoring system in accordance with the present disclosure is configured to monitor.

Turning to FIGS. 5-9, various applications of the exemplary monitoring system are illustrated. In FIG. 5, a monitoring system 16 is deployed in a public restroom facility PR. The monitoring system 16 can be placed near a door in a position to where air flow into/out of the facility may generally be optimized. The monitoring system 16 could also be incorporated into an exhaust air duct of the facility. The monitoring system 16 can be configured to communicate with one or more handheld devices or can establish a permanent or semi-permanent connection to existing communication infrastructure, such as WIFI or the like.

Figure 6:
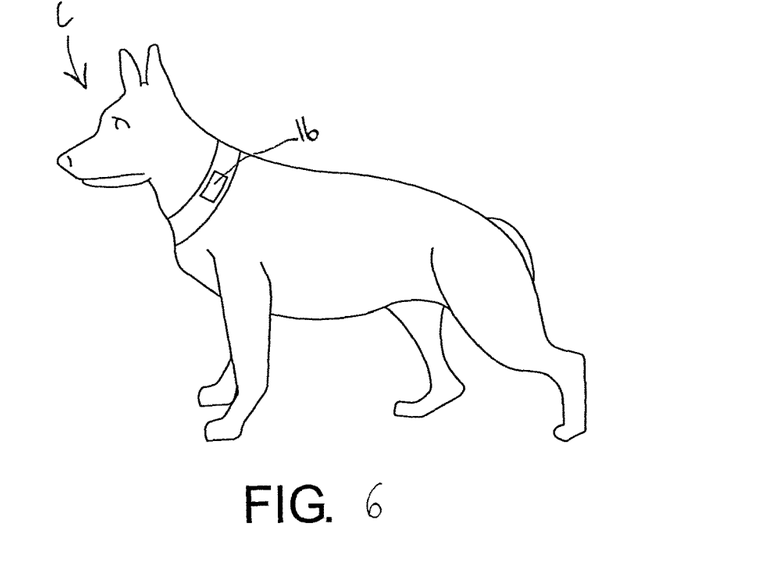
FIG. 6 illustrates an exemplary monitoring system in accordance with the present disclosure integrated into a collar of a law enforcement canine.

In FIG. 6, a monitoring system 16 is integrated into the collar of a law enforcement canine C. It will be appreciated that movement of the canine C will cause air to circulate around the monitoring system 16 to enhance sensing capabilities. In addition, the canine can be instructed to enter certain spaces for inspection and/or sampling of the air that would generally not be accessible by other methods. In addition to mounting on a canine, the monitoring system can be mounted on other mobile platforms such as drones or unmanned or manned vehicles.

Figure 7:
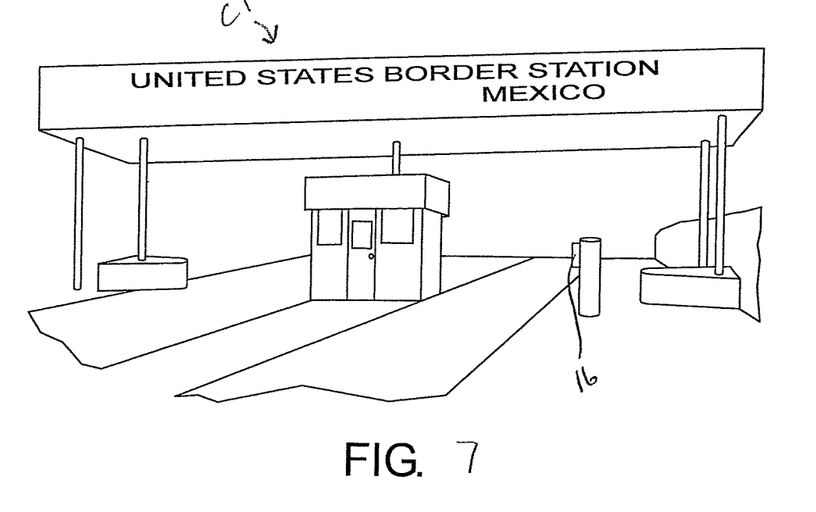
FIG. 7 illustrates another exemplary public space in which the monitoring system in accordance with the present disclosure is configured to monitor.

FIG. 7 illustrates a monitoring system 16 in a customs and/or border patrol checkpoint CP. It will be appreciated a plurality of monitoring systems can be deployed in suitable locations throughout the checkpoint. In the illustrated embodiment, the monitoring system is shown on a post adjacent a vehicle travel path.

Figure 8:
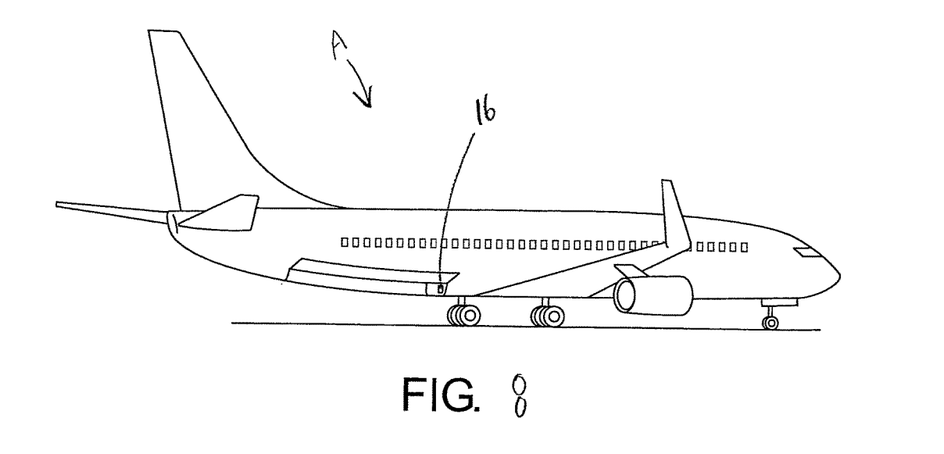
FIG. 8 illustrates an exemplary monitoring system in accordance with the present disclosure integrated into a cargo hold of an aircraft.

FIG. 8 illustrates a monitoring system 16 in a cargo hold of an aircraft A, such as a commercial airliner.

Figure 9:
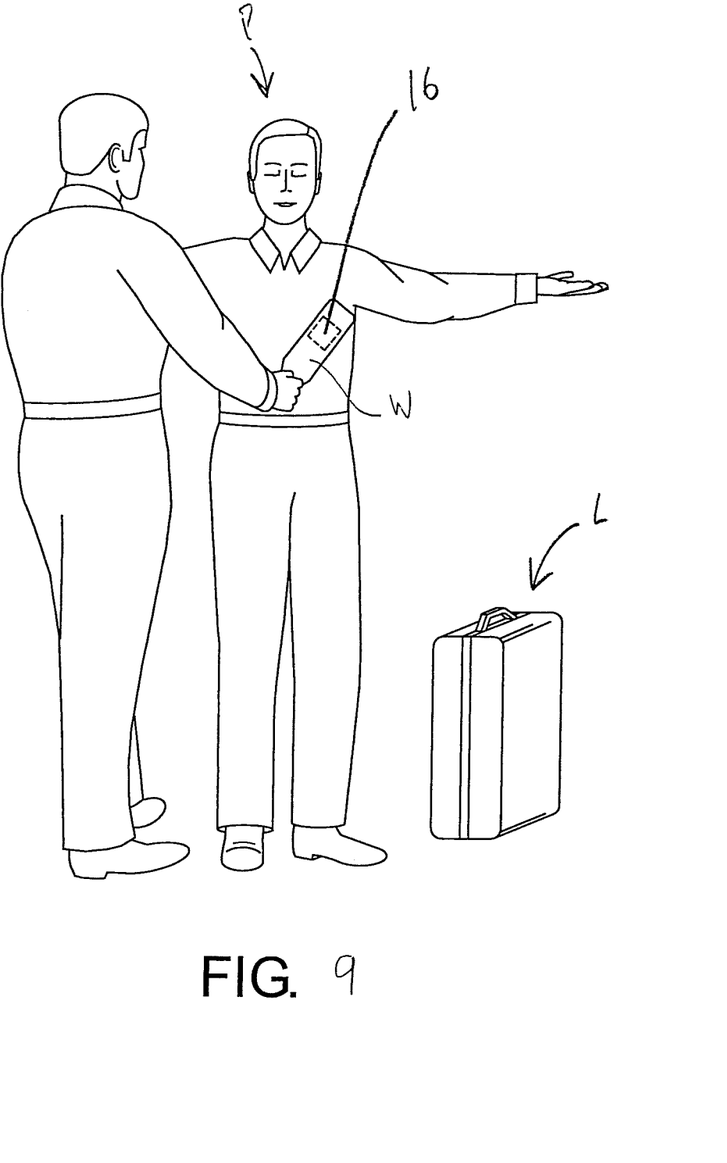
FIG. 9 illustrates an exemplary monitoring system in accordance with the present disclosure integrated into a handheld wand for scanning passengers and/or luggage.

FIG. 9 illustrates a monitoring system 16 integrated into a handheld wand W for manually scanning/sampling a passenger P and the passenger's luggage L. It will be appreciated that the monitoring system 16 can be incorporated into existing wands, such as metal detector wands typically used by security personnel for scanning passengers at airports or other individuals.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A monitoring device for monitoring an environment, the monitoring device comprising a housing and operative to generate data in response to the presence of at least one detected chemical in the environment and communicate the data to an associated receiver for processing by the associated receiver for the detection of one or more chemical signatures in the data;
    wherein the monitoring device includes a detector component, communication circuitry and a power source operatively coupled to the detector component and the communication circuitry for supplying power thereto, and wherein the communication circuitry is configured to transmit data to the associated receiver; and
    wherein the power source includes an antenna configured to receive energy wirelessly and directly supply the received energy to at least one of the detector component or the communication circuitry whereby no onboard battery is used for operation of the monitoring device:
    wherein the monitoring device is configured to periodically activate to sense for the presence of one or more chemicals regardless of whether the monitoring device is connected to the associated receiver:
    wherein the monitoring device transmits past data gathered by the monitoring device when the monitoring device is connected to the associated receiver; and
    wherein at least one of the detector component, communication circuitry or power source is part of a removable/replaceable module.

2. The monitoring device of claim 1, wherein the associated receiver includes a personal communication device, and wherein the housing is a protective case attachable to the personal communication device.

3. The monitoring device of claim 2, wherein at least one of the detector component, communication circuitry or power source is part of a removable/replaceable module selectively attachable to the protective case.

4. The monitoring device of claim 1, wherein the power source further comprises a photovoltaic cell.

5. The monitoring device of claim 1, wherein the housing is a housing of a peripheral device, said peripheral device configured to be used in conjunction with said associated receiver.

6. The monitoring device of claim 1, further comprising an airflow induction device for directing airflow to the detector component.

7. The monitoring device of claim 1, wherein the housing is associated with at least one of an animal collar or muzzle, a vehicle, or a checkpoint.

8. A system comprising: a receiver having a processor and communication circuitry; and a peripheral device having a monitoring device for monitoring an environment, the monitoring device operative to generate data in response to the presence of at least one chemical in the environment and communicate the data to the receiver;
    wherein the processor of the receiver processes the data received from the monitoring device to determine at least one of the kind or concentration of the at least one chemical in the environment;

wherein the monitoring device includes a detector component, communication circuitry and a power source; and wherein the power source includes an antenna configured to receive energy wirelessly and directly supply the received energy to at least one of the detector component or the communication circuitry, whereby no onboard battery is used for operation of the monitoring device;

wherein the monitoring device is configured to periodically activate to sense for the presence of one or more chemicals regardless of whether the monitoring device is connected to the receiver;

wherein the monitoring device transmits past data gathered by the monitoring device when the monitoring device is connected to the receiver; and wherein at least one of the detector component, communication circuitry or power source is part of a removable/replaceable module.

9. The system of claim 8, wherein at least one of the detector component, communication circuitry or power source is part of a removable/replaceable module selectively attachable to the peripheral device.

10. The system of claim 8, wherein the receiver includes a non-transitory computer readable medium storing instructions causing the processor to execute an application for processing the data, the application configured to:
 receive the data from the monitoring device; and
 analyze the data to detect one or more chemical signatures.

11. The system of claim 8, wherein the peripheral device includes a protective case selectively attachable to the receiver.

12. The system of claim 11, wherein the protective case includes a resilient material for cushioning the receiver.

13. The system of claim 8, wherein the receiver is remotely located from the peripheral device.

14. The system of claim 8, wherein the power source further comprises a photovoltaic cell.

15. The system of claim 8, further comprising an airflow induction device for directing airflow to the detector component.

16. A method of detecting a chemical comprising:
 generating data with a monitoring device operative to generate data in response to the presence of at least one chemical in a monitored environment;
 communicating the data to a receiver;
 analyzing the data with the receiver to detect one or more chemical signatures; wherein the monitoring device includes a detector component, communication circuitry and a power source; and
 wherein the power source includes an antenna configured to receive energy wirelessly and directly supply the received energy to at least one of the detector component or the
 communication circuitry, whereby no onboard battery is used for operation of the monitoring device;
 wherein the monitoring device is configured to periodically activate to sense for the presence of one or more chemicals regardless of whether the monitoring device is connected to the receiver;
 wherein the monitoring device transmits past data gathered by the monitoring device when the monitoring device is connected to the receiver; and
 wherein at least one of the detector component, communication circuitry or power source is part of a removable/replaceable module.

17. The method of claim 16, wherein the receiver is remote and spaced apart from the monitoring device.

18. The method of claim 17, wherein the communicating the data to the receiver is performed wirelessly.

19. The method of claim 16, wherein at least one of WIFI, Bluetooth, NFC is used for communicating the data to the receiver.

20. The method of claim 16, further comprising positioning the monitoring device in or on at least one of an animal collar or muzzle, a vehicle, or a checkpoint.

* * * * *